United States Patent
Gray

(10) Patent No.: US 10,052,357 B2
(45) Date of Patent: Aug. 21, 2018

(54) TOPICAL HEALING AND SCAR TREATMENT COMPOSITION

(71) Applicant: Michael William Gray, Bloomfield Hills, MI (US)

(72) Inventor: Michael William Gray, Bloomfield Hills, MI (US)

(73) Assignee: Michael William Gray, Bloomfield Hills, MI (US)

( * ) Notice: Subject to any disclaimer, the term of this patent is extended or adjusted under 35 U.S.C. 154(b) by 369 days.

(21) Appl. No.: 15/053,334

(22) Filed: Feb. 25, 2016

(65) Prior Publication Data

US 2017/0246232 A1    Aug. 31, 2017

(51) Int. Cl.

| | |
|---|---|
| *A61K 36/00* | (2006.01) |
| *A61K 36/47* | (2006.01) |
| *A61K 9/00* | (2006.01) |
| *A61K 36/23* | (2006.01) |
| *A61K 47/34* | (2017.01) |
| *A61K 47/20* | (2006.01) |
| *A61K 47/12* | (2006.01) |
| *A61K 47/22* | (2006.01) |
| *A61K 47/36* | (2006.01) |
| *A61K 47/10* | (2017.01) |
| *A61K 47/14* | (2017.01) |

(52) U.S. Cl.
CPC ............ *A61K 36/47* (2013.01); *A61K 9/0014* (2013.01); *A61K 36/23* (2013.01); *A61K 47/10* (2013.01); *A61K 47/12* (2013.01); *A61K 47/14* (2013.01); *A61K 47/20* (2013.01); *A61K 47/22* (2013.01); *A61K 47/34* (2013.01); *A61K 47/36* (2013.01)

(58) Field of Classification Search
CPC ....................................................... A61K 36/00
USPC ......................................................... 424/725
See application file for complete search history.

(56) References Cited

U.S. PATENT DOCUMENTS

| 7,968,129 B2 | 6/2011 | Golz-Berner et al. |
|---|---|---|
| 2007/0264221 A1 | 11/2007 | Moser et al. |
| 2011/0086060 A1 | 4/2011 | Bidamant et al. |
| 2014/0348873 A1 | 11/2014 | Banov |
| 2014/0350106 A1 | 11/2014 | Banov |

FOREIGN PATENT DOCUMENTS

| CH | 696135 A5 * | 1/2007 |
|---|---|---|
| EP | 2100592 A1 | 9/2009 |
| EP | 2163236 A2 | 3/2010 |

OTHER PUBLICATIONS

Nguyen et al., "The Pathophysiologic Basis for Wound Healing and Cutaneous Regeneration," Biomaterials for Treating Skin Loss, Elsevier, Jan. 28, 2009, pp. 25-55.
Midwood K.S. et al., "Tissue Repair and the Dynamics of the Extracellular Matrix," Int'l. J. Biochemistry and Cell Biology, 36 (2004) 1031-1037.
Stadelmann et al., "Physiology and Healing Dynamics of Chronic Cutaneous Wound," Am. J. Surgery, 176 (2 A. Suppl.): 26S-38S (1998).
Son, et al., "Effects of β-glucan on Proliferation and Migration of Fibroblasts," Current Applied Physics, 5 (5) 468-471 (2005).
Gold et al., "Prevention of Hypertrophic Scars and Keloids by the Prophylactic Use of Topical Silicone Gel Sheets Following a Surgical Procedure in an Office Setting", Dermatol., Surg. 27: 641, (2001).
Sherratt, Jonathan, "Mathematicl Modelling of Scar Tissue Formation," Department of Mathematics, Heriot-Walt University (2010), 3 pages.
Shih et al., "Review of Over-the-Counter Topical Scar Treatment Products," Plastic and Reconstructive Surgery, 119 (3): 1091-1095, (2007).
Paternoster et al., "Meta-Analysis of Genome-Wide Association Studies Identified Three New Risk Loci for Atopic Dermatitis," Nature Genetics, 44 (2) pp. 187-192 (2011).
"Questions and Answers about Psoriasis", National Institute of Arthritis and Musculoskeletal and Skin Diseases, Oct. 2013, (U.S. Department of Health and Human Services), 7 pages.

* cited by examiner

*Primary Examiner* — Michael V Meller
(74) *Attorney, Agent, or Firm* — Brooks Kushman P.C.

(57) ABSTRACT

Topical aqueous compositions are effective in minimizing scar formation and improving the visual appearance of scars. The compositions are also effective in treating numerous skin disorders, including acne, psoriasis, and eczema.

20 Claims, 9 Drawing Sheets

FIG. 4A
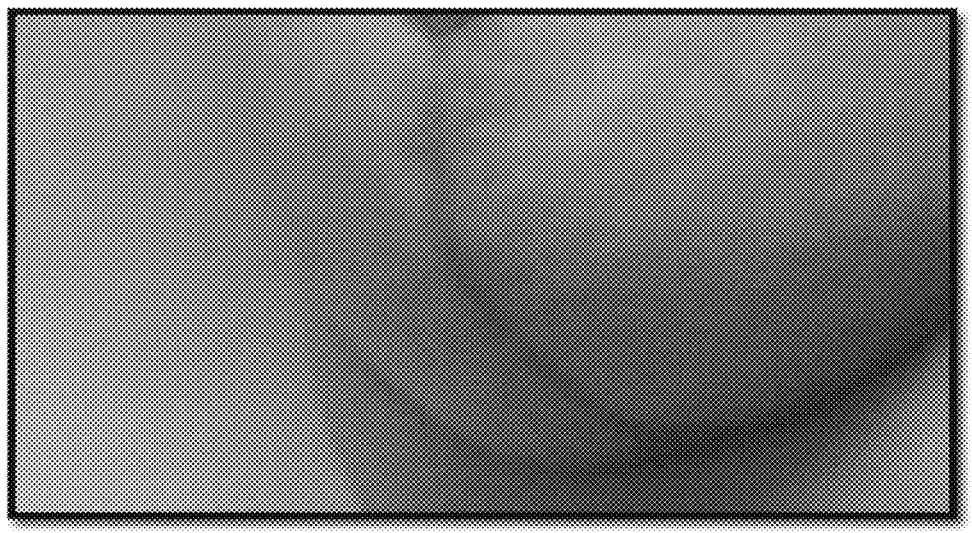
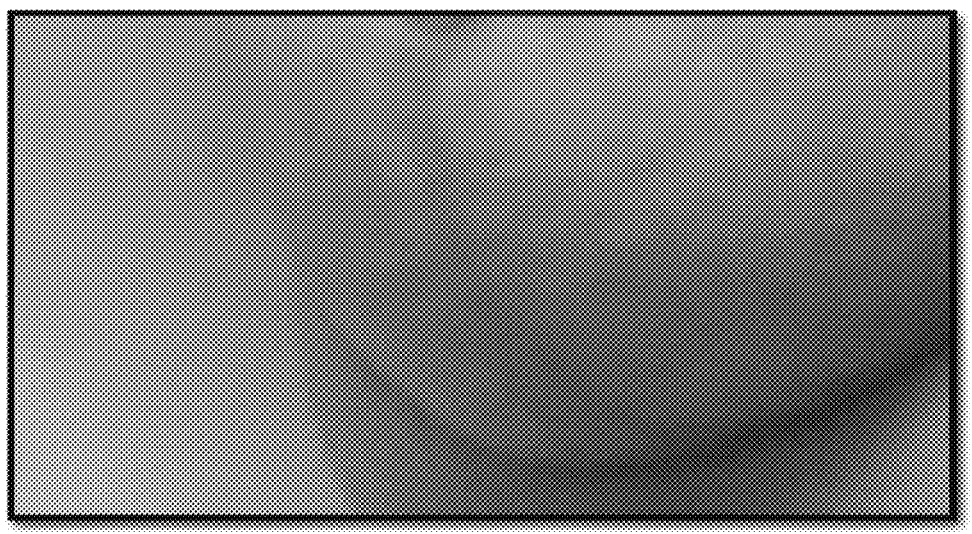
FIG. 4B

FIG. 5A
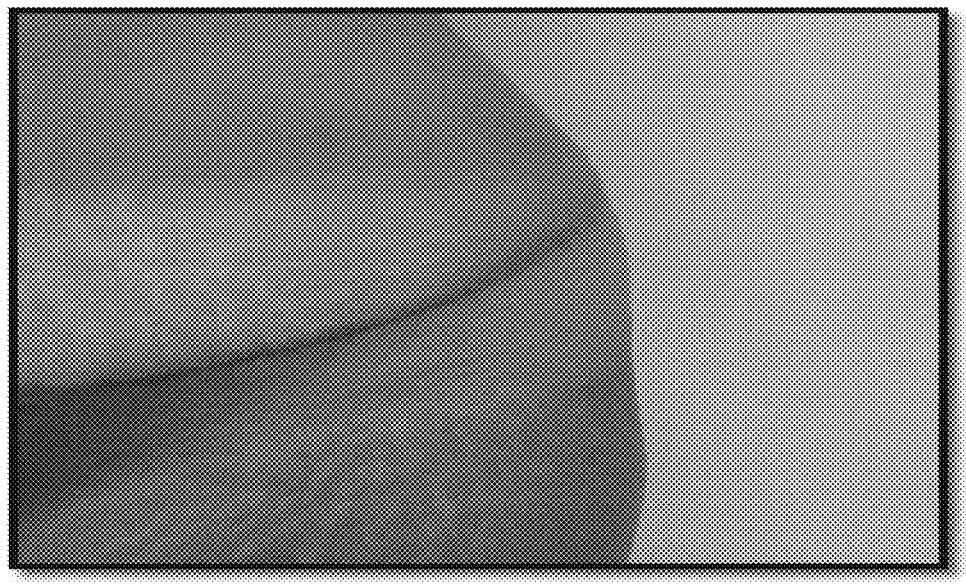
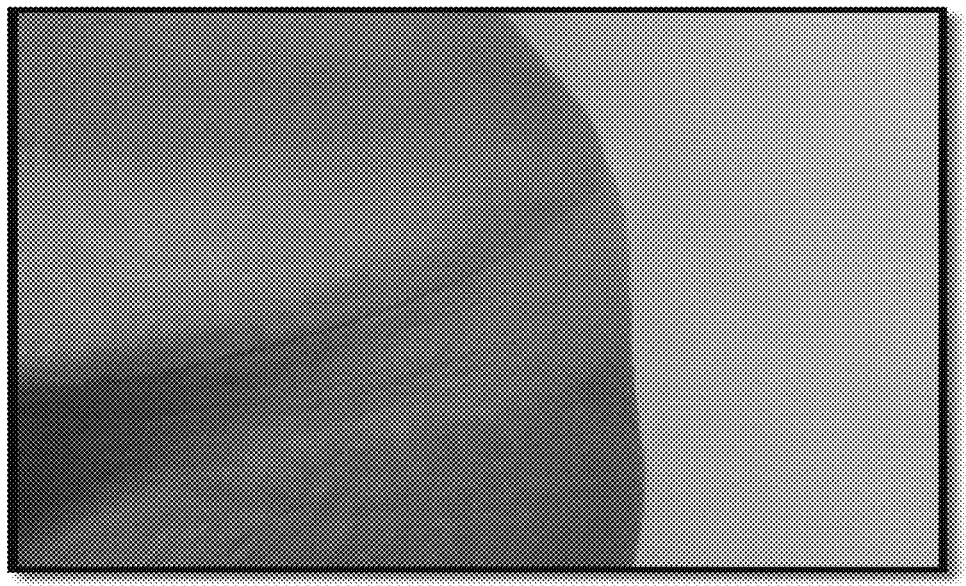
FIG. 5B

Surgical Scar 6 months post surgical

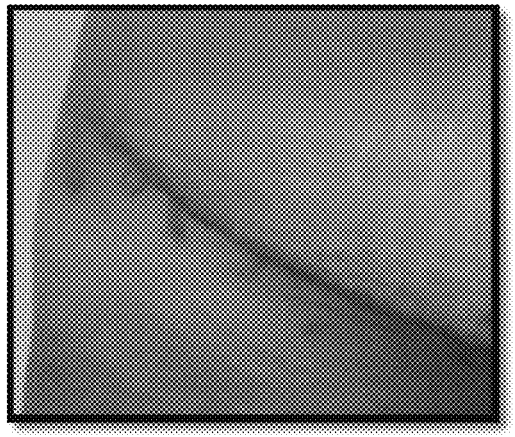
FIG. 7A — Surgical Scar
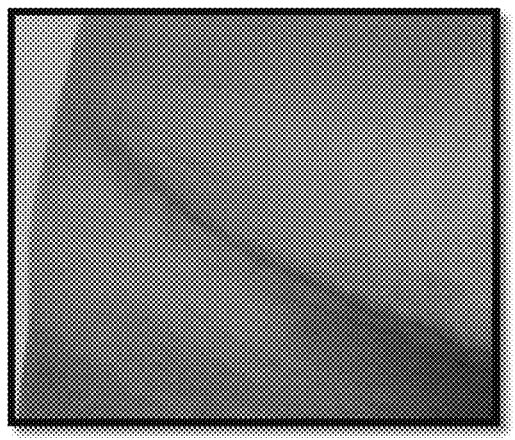
FIG. 7B — 3 months post surgical
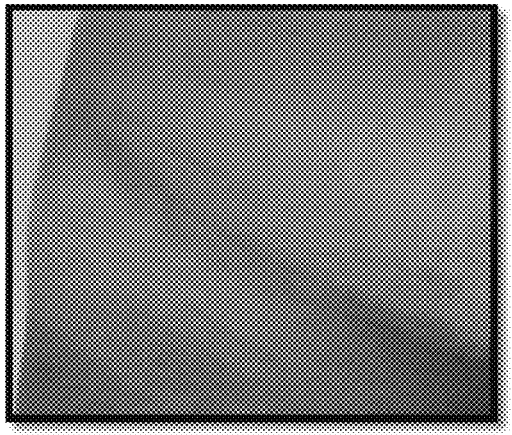
FIG. 7C — 6 months post surgical

TOPICAL HEALING AND SCAR TREATMENT COMPOSITION

BACKGROUND OF THE INVENTION

1. Field of the Invention

The present invention pertains to topical compositions which aid in the healing of wounds.

2. Description of the Related Art

While some of the lower vertebrates are able to regenerate tissue without scarring, e.g. salamanders, with the exception of repair of the endometrium, wounds to human tissue, and particularly skin, are always accompanied by the production of scar tissue.

Wounds may be produced in numerous ways, by burns, punctures, abrasion or tearing of the skin, and by surgery. The mechanism of wound healing has been intensively studied, and is very complex. Some studies have classically divided the healing process into four considerably overlapping phases: hemostasis, inflammation, proliferation, and remodeling. More recently, a division into only two major phases, the early phase and the later phase, has been proposed. "4. The Pathophysiologic Basis For Wound Healing and Cutaneous Regeneration," BIOMATERIALS FOR TREATING SKIN LOSS, Elsevier, Jan. 28, 2009, pp. 25 ff.

Regardless of the theoretical construct used to describe the healing process, all models agree that there is an initial phase involving a clotting cascade, forming a mass of blood platelets aggregated by sticky glycoproteins. Fibrin and fibronectin crosslink to form a plug which traps proteins and particles, and prevents further blood loss. This plug forms the initial main structural support for the wound prior to deposition of collagen. K. S. Midwood, et al., "Tissue Repair and the Dynamics of the Extracellular Matrix," INT'L. J. BIOCHEMISTRY AND CELL BIOLOGY, 36 (6) 1031-1037. This plug is eventually lysed and replaced with granulation tissue.

At a later stage aniogenis (neovascularization) begins, accompanied by fibroblast-initiated formulation of granulation tissue and collagen deposition. The collagen is important in holding the wound closed, since the tensile strength of the fibrin-fibronectin clot is only marginal. Near the end of granulation, remaining fibroblasts commit apoptosis, converting granulation tissue from one rich in cells to one consisting principally of collagen. W. K. Stadelmann et al., "Physiology and Healing Dynamics of Chronic Cutaneous Wound," AM. J. SURGERY, 176 (2 A. Suppl.): 265-385 (1998). This process forms the scaffold upon which reepithelialization takes place. Basal keratinocytes from the wound edges form epithelial cells which migrate in a sheet across the wound site. The more quickly these cells proliferate and migrate, the less scar formation is observed. H. J. Son, et al., "Effects of β-glucan on Proliferation and Migration of Fibroblasts," CURRENT APPLIED PHYSICS, 5 (5) 468-71 (2005).

Scarring is a natural part of the healing process. Scar tissue differs from normal tissues in several ways. For example, sweat glands and hair follicles are exceptionally deficient or totally absent. Moreover, while scar tissue is composed of collagen protein just like normal tissue, the collagen fibers of scar tissue crosslink during fibrosis to form a structure with pronounced alignment of fibers, whereas in normal tissue, a basketweave of collagen fibers is present. J. A. Sheralt, "Mathematical Modeling of Scar Tissue Formation," Department of Mathematics, Heriot-Walt University (2010).

A conclusion which can be reached, is that scar formation can be minimized by rapid reepithelization. However, for this to occur, conditions must be established which promote the proliferation of epithelial cells and their migration. One proposed solution to this problem is to cover the wound with a hydrophobic substance with little water permeability. Silicone gels, silicone sheets, and oleaginous substances such as mineral oils and petrolatum-based ointments have been proposed for this purpose. However, the effect of such products is less than desired. One study found that there was no significant improvement in patients not at high risk for scarring. M. H. Gold, "Prevention of Hypertrophic Scars and Keloids by Prophylactic Use of Topical Silicone Gel Sheets Following a Surgical Procedure in an Office Setting," DERMATOL. SURG. 27: 641, (2001).

The problem with an occlusive approach to increase reepithelization is that while escape of the moisture present in the wound is decreased, the dressings do not allow external moisture to enter the wound, and that there is no mechanism for increasing the moisture content of the wound from the body tissue and blood vessels, i.e. from within. Nor do such treatments favor the production of the myriad of growth factors which are involved in wound healing.

A variety of herbal and alternative medicines have been proposed, including the use of extract from the bark of *Spathodea campanulata beauv*, titrated extracts of *Cemtelia asratica, Anogeissus latifola* bark extract, and *Channa striatus* fish extract combined with cetrimide cream, but no clinical trials had been reported. Topical onion skin extract (Mederma™, Merz Pharmaceuticals) proposes to reduce scarring, but has not been shown to produce any improvement as compared to petrolatum emollient. R. Shih, M. D., et al. "Review of Over-The-Counter Topical Scar Treatment Products," PLASTIC AND RECONSTRUCTIVE SURGERY 119 (3): 1091-5 © 2007.

It would be desirable to provide a topical composition which exhibits moisture retention, encourages production of additional moisture in situ, and also encourages the proliferation and migration of epithelial cells.

Eczema, sometimes called "dermatitis," is a little understood skin inflammation characterized by itchy, erythematous, vesicular, weeping, and crusty patches. Eczema may be triggered by allergic reactions to specific allergens. However, it is believed to be at least partially genetic, and recent studies have identified several genetic variants associated therewith. L. Paternoster, et al., "Meta-analysis of Genome-wide Association Studies Identified Three New Risk Loci For Atopic Dermatitis," NATURE GENETICS 44 (2) pp. 187-82, (2011). Treatment generally involves topical corticosteroids or topical immunosuppressants. However, long term use of such compositions is problematic. Ultraviolet light therapy has also been recommended, but extensive treatment may be expected to increase the risk of skin cancer.

Psoriasis is another not well understood skin disease, characterized by patches of abnormal skin. The most common form is plaque psoriasis, symptoms of which include raised areas of inflamed skin covered with scaly white or silvery skin. Psoriasis is also thought to have a genetic causation factor, and is considered to be an autoimmune disease. "Questions and Answers about Psoriasis," NATIONAL INSTITUTE OF ARTHRITIS AND MUSCULOSKELETAL AND SKI DISEASES, October 2013. No cure is known to exist, but symptoms can be lessened with topical corticosteroids, vitamin D analogs, and especially combinations of these. Moisturizers and emollients such as mineral oil and petrolatum have been found to increase clearance of plaques, especially in conjunction with phototherapy. Curiously, daily baths in the Dead Sea for an extended period (4 weeks) with sun exposure have shown 75% decreased symptoms and remission for several months. Unfortunately, such treatment is not available to most. Systemic treatments are available and being strongly pursued, but most require regular blood and liver function tests to assess toxicity.

It would be desirable to provide a topical composition with little or no toxicity, which can be tolerated for long periods of time, and which reduces the symptoms of eczema and psoriasis.

SUMMARY OF THE INVENTION

It has now been surprisingly and unexpectedly discovered that an aqueous composition containing oils from *Plukenetia volubilis*, extract of *Peucedanum ostruthium*, dimethylsulfoxide, a hydroxycarboxylic acid, niacinamide, hyaluronic acid or salt thereof, an organopolysiloxane, and preferably a gel-forming non-ionic surfactant, together with other ingredients as described below, is effective to increase the healing rate of wounds and thus reduce scar formation. The composition also very surprisingly and unexpectedly reduces the symptoms of eczema and psoriasis.

BRIEF DESCRIPTION OF THE DRAWINGS

The figures are monochrome photographs derived by monochromatizing color photographs.

FIGS. 4A and 4B illustrate a surgical scar shortly after its formation post-surgery, and after six months of treatment with the inventive composition of Example 1.

FIGS. 5A and 5B illustrate a surgical scar shortly after its formation post-surgery, and after six months of treatment with the inventive composition of Example 1.

FIGS. 7A, 7B, and 7C illustrate a surgical scar shortly after its formation post-surgery, and after three and six months of treatment with the inventive composition of Example 1.

DETAILED DESCRIPTION OF THE PREFERRED EMBODIMENTS

Figure 1A:
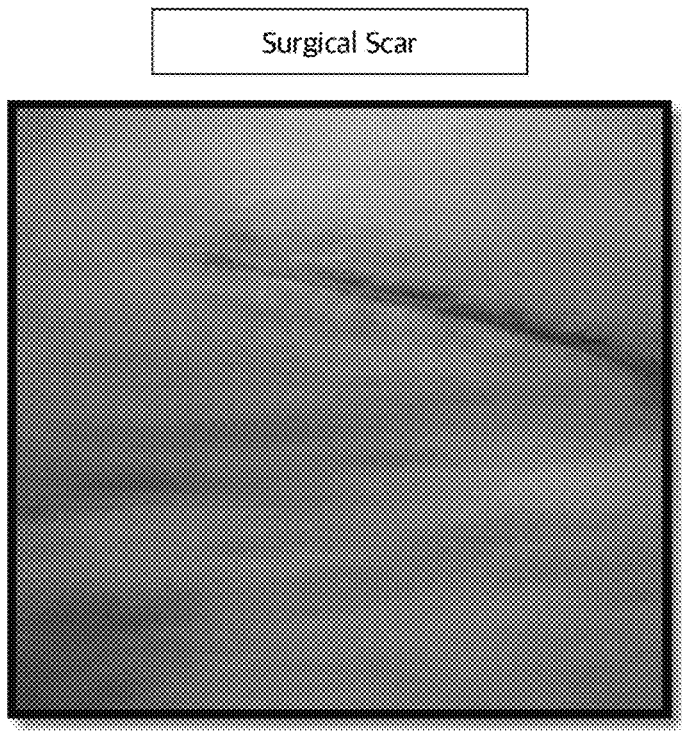
FIGS. 1A and 1B illustrate a surgical scar shortly after its formation post-surgery, and after eight months of treatment with the inventive composition of Example 1.
Figure 1B:
Figure 2A:
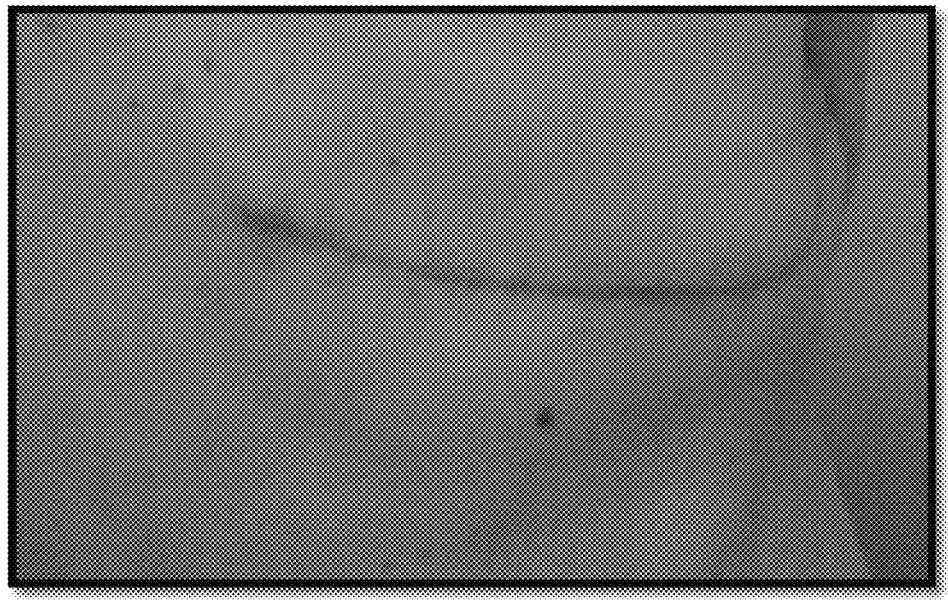
FIGS. 2A and 2B illustrate a surgical scar shortly after its formation post-surgery, and after six months of treatment with the inventive composition of Example 1.
Figure 2B:
Figure 3A:
FIGS. 3A and 3B illustrate a C-section scar shortly after its formation post-surgery, and after six months of treatment with the inventive composition of Example 1.
Figure 3B:
Figure 6A:
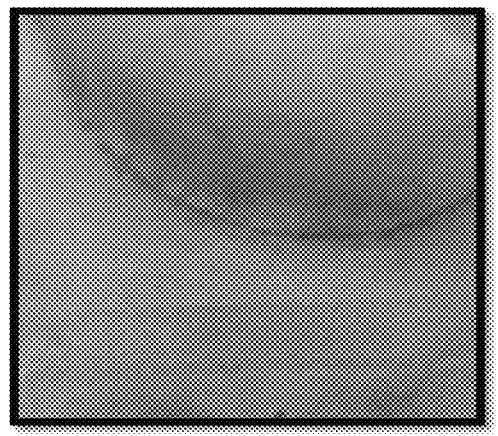
FIGS. 6A and 6B illustrate a surgical scar shortly after its formation post-surgery, and after six months of treatment with the inventive composition of Example 1.
Figure 6B:
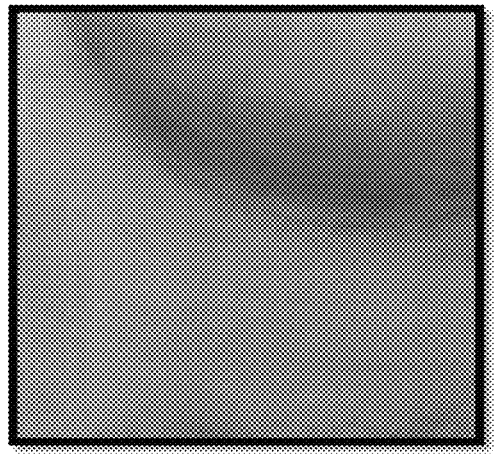

It should be noted that the inventive composition contains numerous ingredients, each of which is believed to have a function. Some of the ingredients are necessary ingredients per se, while others may be substituted in whole or in part by other ingredients having the same function. In the inventive compositions, the ingredients have a synergistic effect which is not obtainable with other combinations of ingredients. Moreover, the believed functions of the necessary ingredients are often unique in the inventive composition.

*Plukenetia volubilis* seed oil is a necessary ingredient, and is commercially available in pharmaceutical/cosmetic quality. The *Plukenetia volubilis* oil is believed to serve as an antioxidant and emollient, and in the inventive formulation, exhibits skin smoothing properties, aids in maintaining skin elasticity, and protects all membranes.

*Peucedanum ostruthium* extract is a necessary ingredient, and is also commercially available. *Peucedanum ostruthium* aids in soothing and protecting skin wounds, and promotes healing. Cellular regeneration, cell function restoration, stressed skin repair, and relieving of skin irritation are believed to be some of its functions.

A polyorganosiloxane is a necessary component. The polyorganosiloxane may be selected from a variety of polyorganosiloxanes, but those bearing in-chain dimethylsiloxy groups and terminal hydroxydimethylsilyl or trimethylsilyl groups, particularly the latter, are preferred. Polydimethylsiloxanes also containing long chain alkyl groups are also useful, in particular when greater hydrophobicity is desired. The polyorganosiloxanes are not solids, but are gel-like or liquid at room temperature (ca. 25° C.), and are used as a hydrating barrier. They minimize escape of water (moisture) and also serve as a protective barrier.

Dimethylsulfoxide (DMSO) is a necessary ingredient, and assists in penetrating the wound and transporting other ingredients along with it. DMSO also has anti-inflammative effects in the composition, for example reduction of swelling, which relieves the tensile stress on the wound, promoting a thinner and less noticeable scar. It also has bacteriostatic activity, and influences collagen synthesis as well as lowering adhesiveness of blood platelets.

An α-hydroxycarboxylic acid is a necessary ingredient, which assists in penetration of other ingredients and rejuvenates skin by debriding. L-lactic acid is the preferred α-hydroxycarboxylic acid, but other α-hydroxycarboxylic acids can be used as well, either alone, in substitution for, or in addition to lactic acid. Examples include glycolic acid, malic acid, citric acid, and tartaric acid.

Niacinamide is a necessary ingredient. Niacinamide assists in increasing the epidermal permeability barrier and increases biosynthesis of ceramides in human keratinocytes, and increases free fatty acid levels. In the inventive composition, niacinamide stimulates microcirculation in the dermis, and helps mitigate acne and the red marks left behind (post-inflammatory hyperpigmentation). Niacinamide in the inventive formulation helps treat uneven skin tone, and thus renders scar tissue less observable, since scar tissue generally has different pigmentation as compared to normal skin.

Hyaluronic acid or salt thereof is a necessary ingredient which promotes collagen formation and hydration in the inventive composition.

Water is a necessary ingredient. The water is preferably of pharmaceutical grade, e.g. aqua puna. Distilled and deionized water, preferably heated and/or filtered to remove microorganisms, are suitable. The water serves to carry the remaining ingredients, provide an emulsifyable vehicle therefore, and initially helps hydrate the wound and surrounding skin. By "q.s." here is meant as amount of water which raises the total weight percentages of all ingredients to 100% by weight.

A hydroxyl-functional emollient is a preferred ingredient. Such emollients are hydrophilic and thus promote water absorbtion from the ambient air. They have a softening, or plasticizing effect on the skin, and also promote the solubility and/or emulsifyability of the necessary ingredients. The hydroxyl-functional emollients do not contain carboxylic acid groups. A preferred hydroxyl-functional emollient is glycerin (glycerol). However, other hydroxyl-functional emollients may be substituted for glycerin all or in part, or be used in addition to glycerin. Examples are neopentyl glycol, propylene glycol, dipropylene glycol, and tripropylene glycol.

Ethylene glycol and diethylene glycol are not preferred as hydroxyl functional emollients and are not included in the definition of hydroxyl-functional emollients herein. The inventive compositions are preferably free of such glycols.

A non-ionic gel former is a preferred ingredient. The non-ionic gel former is conveniently added in the form of an aqueous gel, where it serves not only to supply all or part of the water needed to provide a stable, easily applied composition, but also serves to modify transport of necessary ingredients into the wound and its surrounds. The non-ionic gel former must be pharmaceutically acceptable. Preferred non-ionic gel formers are polyoxyethylene polyoxypropylene block surfactants such as PLURONIC F127 (BASF), and similar products manufactured by others. These block polyether surfactants are available, for example, as a 20 wt./wt. % aqueous gel, and in other concentrations as well. In addition, similar block surfactants containing long chain alkyl end caps by oxyalkylating with a long chain α-olefin epoxide such as VIKOLOX® 15 ("associative thickeners") can perform a similar function, often with less non-ionic gel former. Further non-ionic gel formers include alkyl cellulose ethers such as methylcellulose, propylcellulose, and 2-hydroxypropylcellulose, saccharide alkyl ethers, and the like.

An antioxidant is a preferred ingredient. A preferred antioxidant is butylated hydroxytoluene ("BHT"). However, other pharmaceutically acceptable antioxidants may be used as well. The antioxidant stabilizes the composition against decomposition, including rancidity. The compositions may occasionally experience high temperatures, for example in warehousing and/or shipping in the summer months in moderate climates, or during the largest part of the year in tropical and sub-tropical climates. The antioxidant may also lower the risk of damage to wound tissue by free radicals.

A vegetable gum thickening agent is a preferred ingredient. Vegetable gums exhibiting a thickening effect are well known, and include, for example, guar gum, locust bean gum, gum tragacanth, gum arabic, agar gum, and xanthan gum. Xanthan gum is preferred. The vegetable gum thickener, in conjunction with the non-ionic gel former and other ingredients, serve to adjust the consistency of the formulation, especially the viscosity.

Antimicrobial agents ("biocides") are preferred ingredients. The biocides must be pharmaceutically (or cosmetically) acceptable in the amounts used. The terms "pharmaceutically acceptable" and "cosmetically acceptable" should be treated as synonyms herein. The biocides serve to keep the composition free of microorganisms to avoid spoilage, or the possibility of causing infection of the wound, but also provide biocidal action in the wound itself. Propylparaben and methylparaben and mixtures thereof are preferred. Methylparaben is particularly preferred, as it is easily absorbed.

Emulsifying agents, defined as being other than the hydroxyl-functional emollient and other than the non-ionic gel-former, are preferred ingredients. These ingredients will sometimes be necessary to maintain a stable or metastable emulsion. A stable emulsion is preferred, and is an emulsion which exhibits little or no phase separation upon 3 months storage at 25° C. A metastable emulsion is an emulsion which exhibits some visual phase separation after the same or a shorter period, but can be re-emulsified by simple shaking.

The emulsifying agents are pharmaceutically and/or cosmetically acceptable in the amounts used. Examples include a variety of non-ionic polyoxyethylene surfactants such as polyoxyethylene glycols, polyoxyethylated amines such as a 15 mol oxyethylate of cocamine, oxyethylated fatty acids, anionic surfactants such as sodium lauryl sulfate, and others. Suitable acceptable emulsifying surfactants may be found in the HANDBOOK OF PHARMACEUTICAL EXCIPIENTS, 7$^{th}$ Ed., Pharmaceutical Press, and other treatises as well. Preferred emulsifiers are sodium lauryl sulfate and PEG-15 cocamine, which are preferably used together.

Benzoic acid is a preferred ingredient, and assists in preventing infection as well as decreasing skin irritation and inflammation.

A fragrance is an optional ingredient. The fragrance must be cosmetically acceptable and must not alter the suitability of the formulation for its intended use, nor interfere with the ability to form a stable formulation. Preferred fragrances are natural oils with a strong odor, which allows them to be used in minor amounts. Examples include both natural and synthetic oils or resins such as patchouli, sandalwood, myrrh, frankincense, rose, camellia, etc.

The amounts of the necessary and preferred ingredients are selected so as to form a spreadable cosmetic composition. The composition can be in any stable/metastable form, including without limitation, an aqueous emulsion, a lotion, cream, or gel. The composition may have a Newtonian viscosity with respect to stress, or may be thixotropic or dilatant. The composition may be transparent or opaque (including partially opaque) The composition should not increase in consistency at temperatures as low as, for example 10° C., and should remain sufficiently viscous, pasty, etc., so as to remain easily spreadable at higher temperatures, e.g. up to about 40° C., as well. By the term "liquid form" is meant any form which is spreadable without damage to the skin. This includes, in particular, compositions which one skilled in the art would consider to be a cream, lotion, paste, or gel.

The ingredients may be mixed in any order which is able to provide the desired product consistency, but in general, the more hydrophobic and/or oily ingredients are first mixed together, and then the more hydrophilic ingredients may be added.

The amount of each ingredient may vary. Preferred, more preferred, and most preferred ranges of ingredients are set forth in the Table below. All percentages are by weight, and total 100% relative to all ingredients, including those not listed. Water is always present, and generally constitutes the remainder of the formulation, other than ingredients a)-g) and i) through o).

TABLE 1

| Ingredient | Preferred | More Preferred | Most Preferred |
|---|---|---|---|
| a) *Plukenetia volubilis* | 0.5-6.0 | 1.0-4.0 | 2.0-3.0 |
| b) *Peucedanum ostruthium* | 0.5-4.5 | 1.0-3.0 | 1.5-2.5 |

TABLE 1-continued

| Ingredient | Preferred | More Preferred | Most Preferred |
|---|---|---|---|
| c) Polyorganosiloxane(s) | 2.0-10.0 | 3.0-7.-0 | 4.5-5.5 |
| d) DMSO | 1.0-10.0 | 2.0-6.0 | 4.0-5.5 |
| e) α-hydroxycarboxylic acid(s) | 2.0-12.0 | 4.0-8.0 | 5.0-7.0 |
| f) niacinamide | 0.5-6.0 | 1.0-4.0 | 2.0-3.0 |
| g) hyaluronic acid/salt(s) | 0.001-1.0 | 0.001-0.2 | 0.001-0.005 |
| h) water | >0, q.s. | >0, q.s. | >0, q.s. |
| i) hydroxyl-functional emollient(s) | 4.0-20.0 | 7.0-16.0 | 10.0-12.0 |
| j) non-ionic gel former[1](s) | 40.0-75.0 | 50.0-70.0 | 55.0-65.0 |
| k) antioxidant(s) | 0-3.0 | 0.2-2.0 | 0.3-1.0 |
| l) vegetable gum(s) | 0-2.0 | 0.1-1.0 | 0.2-0.5 |
| m) biocide(s) | 0-2.0 | 0.1-1.0 | 0.15-0.4 |
| n) emulsifying agent(s) | 0-6.0 | 0.1-2.0 | 0.15-1.0 |
| o) benzoic acid | 0-3.0 | 0.1-2.0 | 0.2-1.0 |

[1]As a 20% aqueous gel

The composition has remarkable properties, but these properties may be augmented by the use of the inventive composition as a base composition, to which other active or inactive ingredients are added. Suitable active ingredients, for example, include a variety of growth factors such as epidermal growth factor (EGF), transforming growth factor α (TGF-α), hepatocyte growth factor (HGF), vascular endothelial growth factor (VEGF), platelet derived growth factor (PDGF), fibroblast growth factor, (FGF-1), fibroblast growth factor 2 (FGF-2), transforming growth factor β (TGF-β) and keratinocyte growth factor (KGF). In addition various monoclonal antibodies, corticosteroids, anti-inflammatory agents, immunosuppressants, vitamins (especially C, D, E), testosterone, estradiols, etc. can be added.

In general, since the formulation contains several water-immiscible oils, to form a stable or metastable composition, it will be necessary to include at least one ingredient from the classes of vegetable gum thickener, emulsifier, and non-ionic gel former, preferably ingredients from at least two of these classes, and most preferably ingredients from all three classes.

EXAMPLE

The ingredients from the Table below were admixed to form a homogenous gel.

| Phase | Material | %/w/w |
|---|---|---|
| A | Plukenetia volubilis | 2.888% |
| A | Dimethyl Sulfoxide | 4.796% |
| A | Peucedanum ostruthium | 2.021% |
| A | Silicone Fluid 556 | 5.198% |
| A | Glycerin USP | 11.551% |
| A | Niacinamide USP | 2.599% |
| A | Sodium Hyaluronate | 0.003% |
| A | Butylated hydroxyltoluene | 0.503% |
| A | Propylparaben | 0.201% |
| A | Methylparaben | 0.201% |
| A | Xanthan Gum | 0.347% |
| A | Benzoic Acid | 0.503% |
| B | Lactic Acid USP 88% | 6.064% |
| B | Poloxamer 407 NF Gel 20% | 62.662% |
| B | Ethomeen C/25A | 0.231% |
| B | Calfoam SLS-30 | 0.231% |

The phase A ingredients were introduced into a clean mixing vessel and stirred at medium speed until a homogenous mixture was obtained. The phase B ingredients were then added in order at medium mixing speed until a loose gel is obtained. The stirring speed is then altered and stirring continued until obtaining a uniform homogenous gel.

The inventive composition was applied over the wound area of patients having had cosmetic or reconstructive surgery, and the scar resulting from closure of the wound was observed over a period of months. In all cases, use of inventive composition reduced the size of the scars as compared to normal scarring based on years of surgical experience, and improved their pigmentation as well. Other commercial formulations were tried as well, but none exhibited similarly improved results. FIGS. 1-7 illustrate the improvement in scarring obtained by typical treatment, over periods of from six to eight months. The initial scar developed over a period of 1-2 weeks. Scarring and discoloration are clearly evident in each Figure. Following treatment with the composition of Example 1 for six to eight months, the scars are hardly noticeable.

Figures 8A, 8B:
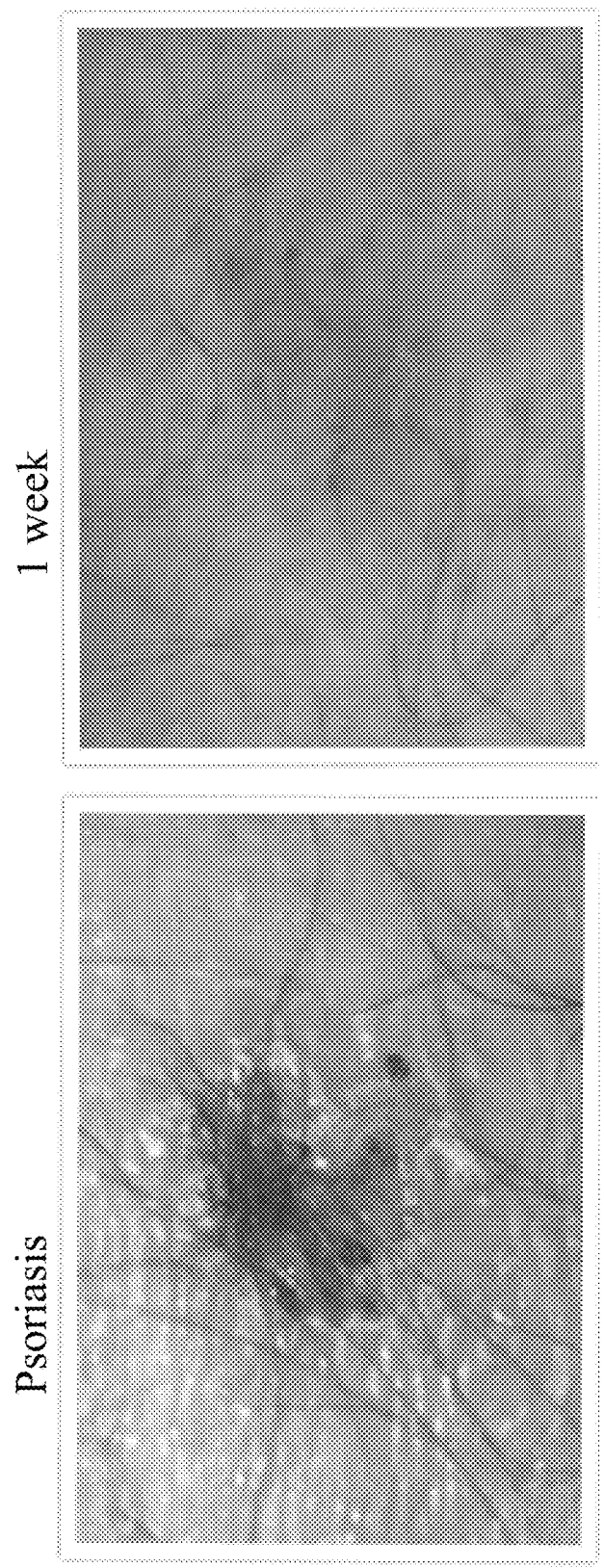
FIGS. 8A and 8B illustrate a dramatic improvement in a psoriasis "lesion" after only one week of treatment with the composition of Example 1.
Figures 9A, 9B, 9C, 9D:
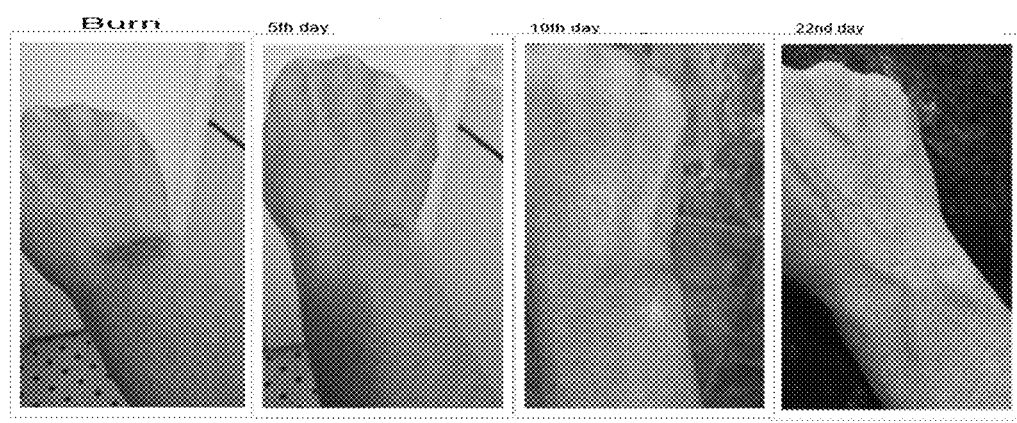
FIGS. 9A, 9B, 9C and 9D illustrate the improvement in a burn scar over an approximately three week period.

The inventive composition also has utility in treating psoriasis and eczema, acne, discoloration and/or scars resulting from acne, and other skin afflictions, such as wrinkles including what are commonly known as "crow's feet," reddened and/or inflamed skin, dry and/or itchy skin. Improvements in patients' conditions have been visually observed. FIG. 8 illustrates improvement in a psoriasis "lesion" or "plaque" after only one week of treatment. The improvement is dramatic. FIG. 9 shows that the inventive composition also minimizes scarring from burns.

In the present invention, the necessary ingredients and preferred ingredients may be used to exclusion of non-necessary ingredients, whether or not these non-necessary ingredients are disclosed herein. In each case, unless the context indicates otherwise, the singular includes the plural. The invention also envisions the combination of ranges disclosed in the preferred, more preferred, and most preferred embodiment ranges. Numerals such as 2 and 2.0 should be considered the same, without implying increased accuracy by the numeral 0.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A composition for increasing the healing rate of wounds and thus reducing scar formation and/or reducing the symptoms of eczema and psoriasis consisting essentially of therapeutically effective amounts of:
    *Plukentia volubilis* seed oil;
    *Peucedanum ostruthium* extract;
    polyorganosiloxane oil;
    dimethylsulfoxide;
    α-hydroxycarboxylic acid;
    niacinamide;
    water;
    hyaluronic acid or a salt thereof; and
    an ingredient selected from at least one of the group consisting essentially of glycerin, neopentyl glycol, propylene glycol, dipropylene glycol, triprolylene glycol, ethylene glycol, diethylene glycol, butylated hydroxytoluene, propylparaben, methylparaben, benzoic acid, epidermal growth factor, transforming growth factor α, hepatocyte growth factor, vascular endothelial growth factor, platelet derived growth factor, fibroblast growth factor, fibroblast growth factor 2, transforming growth factor β, keratinocyle growth factor, vitamin C, vitamin D, vitamin E, testosterone, and estradiol.

2. The composition of claim 1, wherein the *Plukentia volubilis* seed oil ranges from 0.5 to 6 weight percent relative to a total weight of the composition, the *Peucedanum ostruthium* extract ranges from 0.5 to 4.5 weight percent relative to the total weight of the composition, the polyorganosiloxane oil ranges from 2 to 10 weight percent relative to the total weight of the composition, the dimethylsulfoxide ranges from 1 to 10 weight percent relative to the total weight of the composition, the α-hydroxycarboxylic acid ranges from 2 to 12 weight percent relative to the total weight of the composition, the niacinamide ranges from 0.5 to 6 weight percent relative to the total weight of the composition, and the hyaluronic acid or salt thereof ranges from 0.001 to 1 weight percent relative to the total weight of the composition.

3. The composition of claim 1, wherein the *Plukentia volubilis* seed oil ranges from 1 to 4 weight percent relative to a total weight of the composition, the *Peucedanum ostruthium* extract ranges from 1 to 3 weight percent relative to the total weight of the composition, the polyorganosiloxane oil ranges from 3 to 7 weight percent relative to the total weight of the composition, the dimethylsulfoxide ranges from 2 to 6 weight percent relative to the total weight of the composition, the α-hydroxycarboxylic acid ranges from 4 to 8 weight percent relative to the total weight of the composition, the niacinamide ranges from 1 to 4 weight percent relative to the total weight of the composition, and the hyaluronic acid or salt thereof ranges from 0.001 to 0.2 weight percent relative to the total weight of the composition.

4. The composition of claim 1, wherein the *Plukentia volubilis* seed oil ranges from 2 to 3 weight percent relative to a total weight of the composition, the *Peucedanum ostruthium* extract ranges from 1.5 to 2.5 weight percent relative to the total weight of the composition, the polyorganosiloxane oil ranges from 4.5 to 5.5 weight percent relative to the total weight of the composition, the dimethylsulfoxide ranges from 4 to 5.5 weight percent relative to the total weight of the composition, the α-hydroxycarboxylic acid ranges from 5 to 7 weight percent relative to the total weight of the composition, the niacinamide ranges from 2 to 3 weight percent relative to the total weight of the composition, and the hyaluronic acid or salt thereof ranges from 0.001 to 0.005 weight percent relative to the total weight of the composition.

5. The composition of claim 1, wherein the composition is a stable or metastable liquid composition.

6. The composition of claim 1, wherein the composition is one or more of an aqueous emulsion, lotion, cream, and gel.

7. A composition for increasing the healing rate of wounds and thus reducing scar formation and/or reducing the symptoms of eczema and psoriasis consisting essentially of therapeutically effective amounts of:
    *Plukentia volubilis* seed oil;
    *Peucedanum ostruthium* extract;
    polyorganosiloxane oil;
    dimethylsulfoxide;
    α-hydroxycarboxylic acid;
    niacinamide;
    water;
    hyaluronic acid or a salt thereof;
    a hydroxyl-functional emollient selected from at least one of the group consisting essentially of glycerin, neopentyl glycol, propylene glycol, dipropylene glycol, triprolylene glycol;
    butylated hydroxytoluene;
    a biocide selected from at least one of the group consisting essentially of propylparaben and methylparaben; and
    benzoic acid.

8. The composition of claim 7, wherein the *Plukentia volubilis* seed oil ranges from 0.5 to 6 weight percent relative to a total weight of the composition, the *Peucedanum ostruthium* extract ranges from 0.5 to 4.5 weight percent relative to the total weight of the composition, the polyorganosiloxane oil ranges from 2 to 10 weight percent relative to the total weight of the composition, the dimethylsulfoxide ranges from 1 to 10 weight percent relative to the total weight of the composition, the α-hydroxycarboxylic acid ranges from 2 to 12 weight percent relative to the total weight of the composition, the niacinamide ranges from 0.5 to 6 weight percent relative to the total weight of the composition, and the hyaluronic acid or salt thereof ranges from 0.001 to 1 weight percent relative to the total weight of the composition.

9. The composition of claim 7, wherein the *Plukentia volubilis* seed oil ranges from 1 to 4 weight percent relative to a total weight of the composition, the *Peucedanum ostruthium* extract ranges from 1 to 3 weight percent relative to the total weight of the composition, the polyorganosiloxane oil ranges from 3 to 7 weight percent relative to the total weight of the composition, the dimethylsulfoxide ranges from 2 to 6 weight percent relative to the total weight of the composition, the α-hydroxycarboxylic acid ranges from 4 to 8 weight percent relative to the total weight of the composition, the niacinamide ranges from 1 to 4 weight percent relative to the total weight of the composition, and the hyaluronic acid or salt thereof ranges from 0.001 to 0.2 weight percent relative to the total weight of the composition.

10. The composition of claim 7, wherein the hydroxyl-functional emollient ranges from 4 to 20 weight percent relative to a total weight of the composition, the butylated hydroxytoluene is at most 3 weight percent relative to the total weight of the composition, the biocide is at most 2 weight percent relative to the total weight of the composition, and the benzoic acid is at most 3 weight percent relative to the total weight of the composition.

11. The composition of claim 7, wherein the hydroxyl-functional emollient ranges from 7 to 16 weight percent relative to a total weight of the composition, the butylated hydroxytoluene ranges from 0.2 to 2 weight percent relative to the total weight of the composition, the biocide ranges from 0.1 to 1 weight percent relative to the total weight of the composition, and the benzoic acid ranges from 0.1 to 2 weight percent relative to the total weight of the composition.

12. The composition of claim 7, wherein the hydroxyl-functional emollient ranges from 10 to 12 weight percent relative to a total weight of the composition, the butylated hydroxytoluene ranges from 0.3 to 1 weight percent relative to the total weight of the composition, the biocide ranges from 0.15 to 0.4 weight percent relative to the total weight of the composition, and the benzoic acid ranges from 0.2 to 1 weight percent relative to the total weight of the composition.

13. The composition of claim 7, wherein the composition is a stable or metastable liquid composition.

14. The composition of claim 7, wherein the composition is one or more of an aqueous emulsion, lotion, cream, and gel.

15. A composition for increasing the healing rate of wounds and thus reducing scar formation and/or reducing the symptoms of eczema and psoriasis consisting essentially of therapeutically effective amounts of:
*Plukentia volubilis* seed oil;
*Peucedanum ostruthium* extract;
polyorganosiloxane oil;
dimethylsulfoxide;
α-hydroxycarboxylic acid;
niacinamide;
water; and
hyaluronic acid or a salt thereof.

16. The composition of claim 15, wherein the *Plukentia volubilis* seed oil ranges from 0.5 to 6 weight percent relative to a total weight of the composition, the *Peucedanum ostruthium* extract ranges from 0.5 to 4.5 weight percent relative to the total weight of the composition, the polyorganosiloxane oil ranges from 2 to 10 weight percent relative to the total weight of the composition, the dimethylsulfoxide ranges from 1 to 10 weight percent relative to the total weight of the composition, the α-hydroxycarboxylic acid ranges from 2 to 12 weight percent relative to the total weight of the composition, the niacinamide ranges from 0.5 to 6 weight percent relative to the total weight of the composition, and the hyaluronic acid or salt thereof ranges from 0.001 to 1 weight percent relative to the total weight of the composition.

17. The composition of claim 15, wherein the *Plukentia volubilis* seed oil ranges from 1 to 4 weight percent relative to a total weight of the composition, the *Peucedanum ostruthium* extract ranges from 1 to 3 weight percent relative to the total weight of the composition, the polyorganosiloxane oil ranges from 3 to 7 weight percent relative to the total weight of the composition, the dimethylsulfoxide ranges from 2 to 6 weight percent relative to the total weight of the composition, the α-hydroxycarboxylic acid ranges from 4 to 8 weight percent relative to the total weight of the composition, the niacinamide ranges from 1 to 4 weight percent relative to the total weight of the composition, and the hyaluronic acid or salt thereof ranges from 0.001 to 0.2 weight percent relative to the total weight of the composition.

18. The composition of claim 15, wherein the *Plukentia volubilis* seed oil ranges from 2 to 3 weight percent relative to a total weight of the composition, the *Peucedanum ostruthium* extract ranges from 1.5 to 2.5 weight percent relative to the total weight of the composition, the polyorganosiloxane oil ranges from 4.5 to 5.5 weight percent relative to the total weight of the composition, the dimethylsulfoxide ranges from 4 to 5.5 weight percent relative to the total weight of the composition, the α-hydroxycarboxylic acid ranges from 5 to 7 weight percent relative to the total weight of the composition, the niacinamide ranges from 2 to 3 weight percent relative to the total weight of the composition, and the hyaluronic acid or salt thereof ranges from 0.001 to 0.005 weight percent relative to the total weight of the composition.

19. The composition of claim 15, wherein the composition is a stable or metastable liquid composition.

20. The composition of claim 15, wherein the composition is one or more of an aqueous emulsion, lotion, cream, and gel.

* * * * *